United States Patent
Thakur et al.

(10) Patent No.: US 8,858,448 B2
(45) Date of Patent: Oct. 14, 2014

(54) MONITORING PROJECTIONS ALONG PRINCIPAL COMPONENTS OF MULTIPLE SENSORS AS AN INDICATOR OF WORSENING HEART FAILURE

(75) Inventors: Pramodsingh Hirasingh Thakur, White Bear Lake, MN (US); Abhilash Patangay, Inver Grove Heights, MN (US); Ramesh Wariar, Blaine, MN (US); John D. Hatlestad, Maplewood, MN (US); Yi Zhang, Plymouth, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 482 days.

(21) Appl. No.: 13/325,120

(22) Filed: Dec. 14, 2011

(65) Prior Publication Data
US 2012/0157858 A1   Jun. 21, 2012

Related U.S. Application Data

(60) Provisional application No. 61/425,061, filed on Dec. 20, 2010.

(51) Int. Cl.
*A61B 5/02* (2006.01)
*A61B 5/11* (2006.01)
*A61B 5/0205* (2006.01)
*A61B 5/042* (2006.01)
*A61B 5/00* (2006.01)
*A61B 7/02* (2006.01)
*A61B 5/08* (2006.01)
*A61N 1/362* (2006.01)
*A61B 7/04* (2006.01)
*A61N 1/37* (2006.01)
*A61B 5/053* (2006.01)

(52) U.S. Cl.
CPC .............. *A61B 5/042* (2013.01); *A61B 5/1107* (2013.01); *A61B 5/0809* (2013.01); *A61B 5/0205* (2013.01); *A61N 1/3627* (2013.01); *A61B 7/04* (2013.01); *A61N 1/37* (2013.01); *A61B 2562/0219* (2013.01); *A61B 5/053* (2013.01); *A61B 5/6869* (2013.01); *A61B 7/023* (2013.01); *A61B 5/7253* (2013.01)
USPC ........................................................ 600/481

(58) Field of Classification Search
USPC ................................................ 600/481–504
See application file for complete search history.

(56) References Cited

U.S. PATENT DOCUMENTS 6,076,015 A   6/2000   Hartley et al.
6,371,922 B1  4/2002   Baumann et al.

(Continued)

OTHER PUBLICATIONS

Vanderheyden, Marc, et al., "Continuous Monitoring of Intra-thoracic Impedance and Right Ventricular Pressures in Patients with Heart Failure", Circulation: Heart Failure, (Mar. 2010), 29 pgs.

*Primary Examiner* — Patricia Mallari
*Assistant Examiner* — Tiffany Weston
(74) *Attorney, Agent, or Firm* — Schwegman, Lundberg & Woessner, P.A.

(57) ABSTRACT

A device can include at least a first physiologic sensor circuit configured to provide a first physiologic signal, a second physiologic sensor circuit configured to provide a second physiologic signal, and a processor circuit. The processor circuit includes a principal component analysis circuit configured to represent data determined from the at least first and second physiologic sensor circuits as at least first and second axes, respectively, in a multidimensional space, determine one or more principal components in the multidimensional space, determine a quantitative attribute of the first and the second physiologic signals using at least one of the determined principal components or a projection of the data along the at least one determined principal component, and provide an indication of heart failure status according to the quantitative attribute to at least one of a user or a process.

20 Claims, 8 Drawing Sheets

(56) References Cited

U.S. PATENT DOCUMENTS

| | | |
|---|---|---|
| 6,409,675 B1 | 6/2002 | Turcott |
| 6,438,409 B1 | 8/2002 | Malik et al. |
| 6,473,646 B2 | 10/2002 | Sun et al. |
| 6,572,557 B2 | 6/2003 | Tchou et al. |
| 6,666,826 B2 | 12/2003 | Salo et al. |
| 6,741,885 B1 | 5/2004 | Park et al. |
| 6,760,622 B2 | 7/2004 | Helland et al. |
| 6,952,611 B2 | 10/2005 | Sun et al. |
| 6,980,851 B2 | 12/2005 | Zhu et al. |
| 7,107,093 B2 | 9/2006 | Burnes |
| 7,225,013 B2 | 5/2007 | Geva et al. |
| 7,457,664 B2 | 11/2008 | Zhang et al. |
| 7,509,170 B2 | 3/2009 | Zhang et al. |
| 7,526,338 B1 | 4/2009 | Gill |
| 7,567,836 B2 | 7/2009 | Zhang |
| 7,629,889 B2 | 12/2009 | Sachanandani et al. |
| 7,706,866 B2 | 4/2010 | Zhang |
| 7,797,036 B2 | 9/2010 | Zhang |
| 7,805,185 B2 | 9/2010 | Zhang et al. |
| 2001/0037067 A1 | 11/2001 | Tchou et al. |
| 2004/0127792 A1 | 7/2004 | Siejko et al. |
| 2004/0148140 A1* | 7/2004 | Tarassenko et al. .......... 702/189 |
| 2005/0216067 A1 | 9/2005 | Min et al. |
| 2006/0089679 A1 | 4/2006 | Zhu et al. |
| 2007/0260285 A1 | 11/2007 | Libbus et al. |
| 2008/0228090 A1 | 9/2008 | Wariar et al. |
| 2009/0005829 A1 | 1/2009 | Mi |
| 2009/0099426 A1 | 4/2009 | Sachanandani et al. |
| 2010/0004712 A1 | 1/2010 | Zhao et al. |
| 2010/0045467 A1 | 2/2010 | Sachanandani et al. |
| 2010/0094102 A1 | 4/2010 | Zhang et al. |
| 2010/0179395 A1* | 7/2010 | Bloem .......................... 600/301 |

* cited by examiner

MONITORING PROJECTIONS ALONG PRINCIPAL COMPONENTS OF MULTIPLE SENSORS AS AN INDICATOR OF WORSENING HEART FAILURE

CROSS-REFERENCE TO RELATED APPLICATIONS

This application claims the benefit of U.S. Provisional Application No. 61/425,061, filed on Dec. 20, 2010, under 35 U.S.C. §119(e), which is incorporated herein by reference in its entirety.

BACKGROUND

Medical devices can include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Medical devices also include ambulatory or wearable medical devices (WMDs) such as wearable cardioverter defibrillators (WCDs). WCDs are monitors that include surface electrodes. The surface electrodes are arranged to provide one or both of monitoring surface electrocardiograms (ECGs) and delivering cardioverter and defibrillator shock therapy.

Some medical devices include one or more sensors to monitor different physiologic aspects of the patient. The devices may derive measurements of hemodynamic parameters related to chamber filling and contractions from electrical signals provided by such sensors. Sometimes patients who are prescribed these devices have experienced repeated heart failure (HF) decompensation or other events associated with worsening HF. Symptoms associated with worsening HF include pulmonary and/or peripheral edema, dilated cardiomyapathy, or ventricular dilation. Early attention to signs and symptoms of HF decompensation is needed for the health of the patient and allows early initiation of treatment.

An approach for detecting HF can be found in Zhao et al., "Systems and Methods for Use by an Implantable Medical Device for Detecting Heart Failure Based on the Independent Information Content of Immitance Vectors," U.S. Patent Publication No. 2010/0004712, filed Jul. 7, 2008.

OVERVIEW

This document relates to systems and methods for monitoring hemodynamic function of a patient or subject, and in particular for improved monitoring of heart failure.

In an example, an apparatus includes at least a first physiologic sensor circuit configured to provide a first physiologic signal, a second physiologic sensor circuit configured to provide a second physiologic signal, and a processor circuit. The processor circuit includes a principal component analysis circuit configured to represent data determined from the first physiologic sensor circuit as a first axis in a multidimensional space and represent data determined from the second physiologic sensor circuit as a second axis in the multidimensional space, determine a plurality of principal components in the multidimensional space, determine a quantitative attribute of the first and the second physiologic signals using at least one of the determined principal components or a projection of the data along the determined principal components, and provide an indication of heart failure according to the quantitative attribute to at least one of a user or a process.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

A medical device (e.g., an IMD or WMD) can include one or more of the features, structures, methods, or combinations thereof described herein. For example, a cardiac monitor or a cardiac stimulator can be implemented to include one or more of the advantageous features or processes described below. It is intended that such a monitor, stimulator, or other implantable or partially implantable device need not include all of the features described herein, but can be implemented to include selected features that provide for unique structures or functionality. Such a device can be implemented to provide a variety of therapeutic or diagnostic functions.

Figure 1:
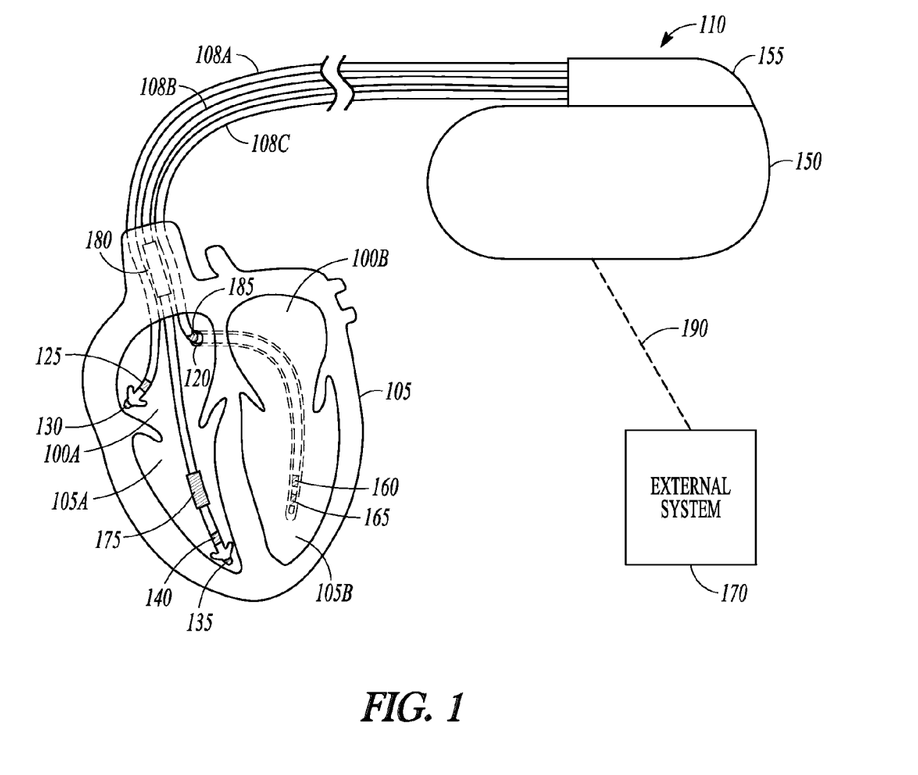
FIG. 1 is an illustration of an example of portions of a system that uses an IMD or other ambulatory medical device.

FIG. 1 is an illustration of an example of portions of a system that uses an IMD 110 or other ambulatory medical device that can be capable of moving about with the subject, such as chronically during activities of daily living. Examples of IMD 110 include, without limitation, a pacer, a defibrillator, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals.

The IMD 110 is coupled by one or more leads 108A-C to heart 110. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes can be electrically coupled to sense amplifiers to sense electrical cardiac signals.

Sensed electrical cardiac signals can be sampled to create an electrogram (sometimes called an egram). An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 can include a third cardiac lead 108C attached to the IMD 110 through the header 155. The third cardiac lead 108C includes ring electrodes 160 and 165 placed in a coronary vein lying epicardially on the left ventricle (LV) 105B via the coronary vein. The third cardiac lead 108C can include a ring electrode 185 positioned near the coronary sinus (CS) 120.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150.

Note that although a specific arrangement of leads and electrodes are shown the illustration, the present methods and systems will work in a variety of configurations and with a variety of electrodes. Other forms of electrodes include meshes and patches which can be applied to portions of heart 105 or which can be implanted in other areas of the body to help "steer" electrical currents produced by IMD 110.

An IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Figure 2:
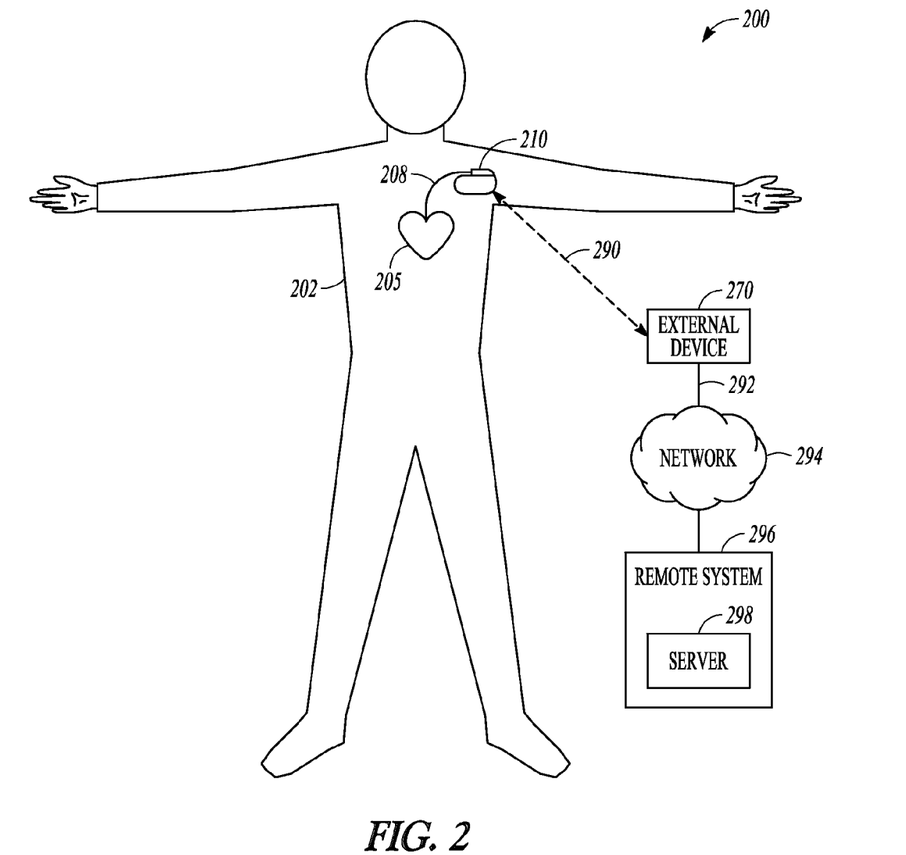
FIG. 2 is an illustration of an example of portions of another system that uses an IMD or other ambulatory medical device.

FIG. 2 is an illustration of an example of portions of another system 200 that uses an IMD or other ambulatory medical device 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicated via the network using a link 292 that can be wired or wireless. In some examples, the remote system 296 provides patient management functions and can include one or more servers 298 to perform the functions.

As explained previously, early attention to signs and symptoms of HF decompensation is needed for optimal health of the patient. Some types of medical devices include multiple sensors that can produce a signal representative of an aspect of physiology related to HF. One of the challenges is to take the output from the multiple sensors and form a composite predictor of progression of HF of a patient. Such a predictor should ensure that actual changes are detected accurately while false alarms are minimized.

Output from the multiple sensors may be related or unrelated to each other during stable HF. For example, if the physiologic signals are representative of similar aspects of the subject's physiology, the physiologic signals will exhibit some degree of relationship to each other during stable HF.

As HF worsens, the relationship between sensor outputs may change. The relationship between physiologic signals representative of similar physiological aspects may weaken because the principal driving forces commonly affecting the sensors (e.g., a circadian rhythm or other intrinsic rhythm) may diminish during worsening HF. Physiologic signals representative of dissimilar physiological aspects may increased relationship due to convergence to the same physiologic state of the subject. Monitoring changes that are reflective or representative of changing relationship between the outputs of multiple sensors can lead to prediction of worsening HF of the subject.

Figure 3:
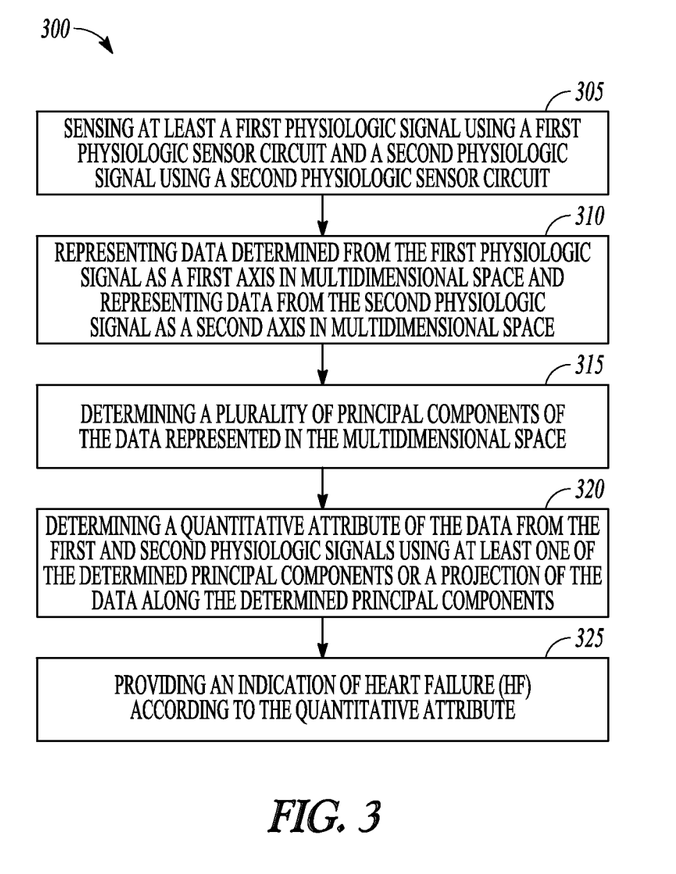
FIG. 3 is a flow diagram of a method of operating an implantable or other ambulatory medical device for detecting HF.

FIG. 3 is a flow diagram of a method 300 of operating an implantable or ambulatory medical device for the purposes of detecting HF of a subject, predicting progression of the HF, or both detecting HF and predicting progression of HF. At block 305, at least a first physiologic signal is sensed using a first physiologic sensor circuit and a second physiologic signal is sensed using a second physiologic sensor circuit.

A physiologic signal includes physiological information of a subject and is representative of some aspect of a subject's physiology. The first physiologic signal and the second physiologic signal can be representative of similar aspects of a subject's physiology, or they can be representative of dissimilar aspects of a subject's physiology.

An example of physiologic signals that are representative of similar aspects includes physiologic signals representative of different parameters of heart sounds. Heart sounds are associated with mechanical vibrations from activity of a subject's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the closing of the aortic valve and the beginning of diastole. The third heart sound (S3) and fourth heart sound (S4) are related to filling pressures of the left ventricle during diastole. A heart sound sensor circuit produces an electrical physiologic signal which is representative of mechanical activity of a patient's heart. The heart sound sensor circuit can be disposed in a heart, near the heart, or in another location where the acoustic energy of heart sounds can be sensed. In some examples, the heart sound sensor circuit includes an accelerometer disposed in or near a heart. In another example, the heart sound sensor circuit includes an accelerometer disposed in the IMD. In another example, the heart sound sensor circuit includes a microphone disposed in or near a heart.

Devices that can measure mechanical vibrations of the heart are likely to be sensitive to other mechanical vibrations such as those arising out of patient activity. Thus heart sound amplitudes measured by these devices may reflect at least a portion of the patient activity. During stable HF, patient activity tends to be high during the day and low to zero during the night. This circadian variability in patient activity level may introduce a common driving force to the amplitudes of all heart sounds introducing a stronger relationship between various heart sound amplitudes or amplitudes of certain portions of a cardiac cycle of heart sound waveform (such as amplitude of R-S2 segment). As HF worsens, patients tend to be less active. This will result in a reduction in the common driving force causing a weakening of the relationship between various heart sounds amplitude. In addition worsening HF may cause S3 amplitude to rise, thus selectively or preferentially affecting the S3 amplitude over other heart sound amplitude. This may further worsen the relationship between S3 amplitude and amplitudes of other heart sounds. An approach for monitoring heart sounds is found in Siejko et al., U.S. Patent Application Publ. No. 2004/0127792, entitled "Method and Apparatus for Monitoring of Diastolic Hemodynamics," filed Dec. 30, 2002, which is incorporated herein by reference in its entirety.

An example of physiologic signals that are representative of dissimilar aspects includes a physiologic signal representative of a heart sound and a physiologic signal representative of intra-thoracic total impedance (ITTI) of the subject. To measure impedance of cardiac or thoracic tissue, a medical device provides current between cardiac electrodes and measures the resulting voltage using the same of different electrodes. The impedance can be determined by the medical device using Ohm's Law (R=V/I).

For example, in FIG. 1 impedance can be measured between coil electrode 175 and an electrode formed on the IMD can 150. This can provide a measure of the impedance across the thorax region of the subject, which is sometimes called intra-thoracic total impedance (ITTI). This measure of impedance can be used as a respiration sensor and can be used to determine minute ventilation. An approach to measuring thoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference.

Returning to the method 300 of FIG. 3, sensor data can be determined from a physiologic signal by sampling of the signal or by deriving the sensor data from the samples obtained from the signal. Changes in relationship between the physiologic signals from multiple sensors can be monitored by representing the sensor data determined from the signals in a multidimensional space. Analysis of this multidimensional space can reveal underlying relationships between the data produced by the sensors.

Figure 4:
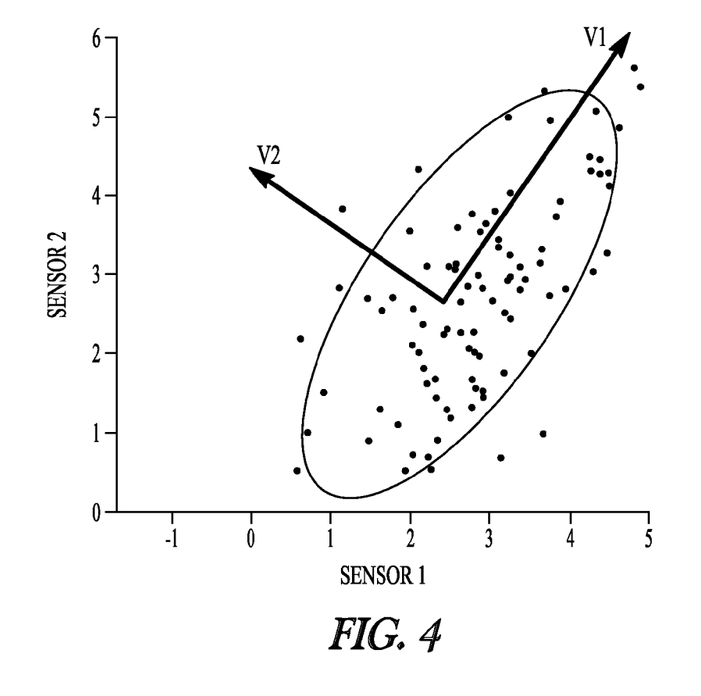
FIG. 4 shows an example of a two-dimensional space formed using data from two sensors.

At block 310, data determined from the first physiologic signal is represented as a first axis in a multidimensional space and data determined from the second physiologic signal is represented as a second axis in the multidimensional space. FIG. 4 shows the simple case of a two-dimensional space formed using data from two sensors, Sensor 1 and Sensor 2. More dimensions can be created by using more sensors or more data derived from sensors. In the Figure, data from Sensor 1 is the horizontal axis and data from Sensor 2 is the vertical axis. A cloud of data points is shown in the multi-dimensional space.

At block 315, a plurality of principal components of the data represented in the multi-dimensional space is determined. In FIG. 4, the principal components are labeled V1 and V2. In general, the principal components of the multi-dimensional space are a set of uncorrelated axes, directions, or orthogonal dimensions within the multi-dimensional space. In some examples, the principal components are sorted (e.g., in descending order) according to the variance of the projections of the data along the uncorrelated axes. The first principal component has as high a variance as possible. In FIG. 4, V1 is the first principal component and has the highest variance. Each succeeding principal component has the next highest variance possible and is constrained to be orthogonal to the preceding principal components. The principal components can be viewed as a subset of all possible eigenvectors in the multidimensional space. The first principal component can be viewed as the eigenvector with the highest eigenvalue.

Figure 5:
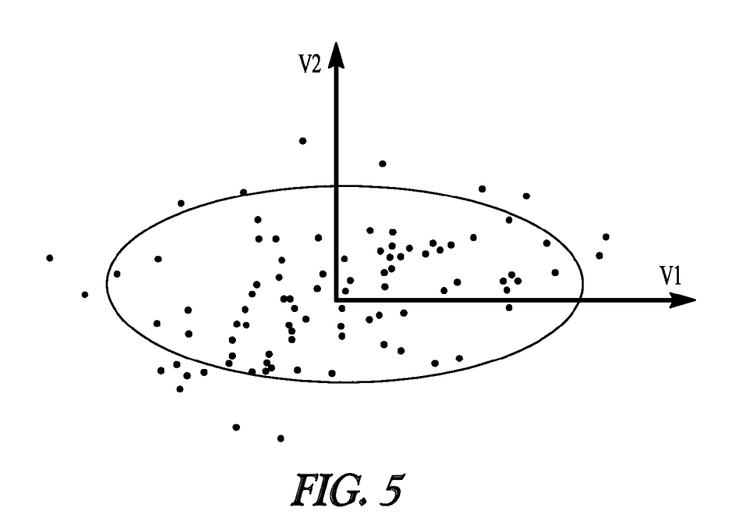
FIG. 5 shows a representation of the uncorrelated axes in a multidimensional space.

Because the principal components are constrained to be orthogonal to each other, they can be used as axes in a transformed multidimensional space. The principal components are transformed to new uncorrelated axes by computing the Karhunen Loeve Transform (KLT, sometimes called the Hotelling transform) of the data. FIG. 5 shows a representation of the uncorrelated axes derived using the KLT.

The eigenvalues of the principal components can be determined from the covariance matrix. For N sensors the covariance matrix would be an N×N matrix. For the case of two sensors or two-dimensions, the 2×2 matrix would be $$\begin{bmatrix} \sigma_x^2 & \rho_{xy} \\ \rho_{xy} & \sigma_y^2 \end{bmatrix} \quad (1)$$

where $\sigma_x^2$ is the variance of the first sensor, $\sigma_y^2$ is the variance of the second sensor, and $\rho_{xy}$ is the correlation between the data from the first physiologic sensor signal and the data from the second physiologic sensor signal.

By applying the KLT, the covariance matrix can be transformed into a diagonal matrix of eigenvalues $$C = \begin{bmatrix} \lambda_{v1} & 0 \\ 0 & \lambda_{v2} \end{bmatrix} \quad (2)$$

where $\lambda_{v1}$ and $\lambda_2$ are eigenvalues of the eigenvectors, or principal components V1 and V2. In a higher dimensional space, more than two principal components and corresponding eigenvalues can be obtained. In general, up to N principal components and corresponding eigenvalues can be obtained in an N-dimensional space.

At block 320, a quantitative attribute of the data is determined from the first and second physiologic signals using at least one of the determined principal components. In some examples, the quantitative attribute includes a measure of ellipticity of a data cloud formed by representing the data from the first and second physiologic signals in the multidimensional space. In some examples, the ellipticity for a group of N sensors can be calculated using $$\text{Ellipticity} = \frac{\lambda_{max}}{\sum \lambda_i} \quad (3)$$

where $\lambda_{max}$ is the highest eigenvalue and $\lambda_i$ is the ith eigenvalue of the N eigenvalues of the N principal components calculated for an N-dimensional space.

As explained previously, the physiologic signals output by the multiple sensors may be representative of similar aspects of physiology or may be representative of dissimilar aspects of physiology. If the physiologic signals represent similar physiology, the data cloud formed in the multi-dimensional space will show some ellipticity during stable HF such as the ellipticity shown in the example of FIG. 4. If the physiologic signals represent dissimilar physiology, the data cloud will show relatively less ellipticity (e.g., the data cloud in FIG. 4 may be more of a circle than an ellipse) during stable HF.

At block 325, an indication of HF is provided to least one of a user or a process according to the quantitative attribute. If the quantitative attribute is ellipticity of the data in the multi-dimensional space, the indication of HF is provided according to the calculated ellipticity. Ellipticity of the data from physiologic signals representative of similar physiology will decrease as HF worsens. In some examples, an indication of worsening HF can be provided when the ellipticity of the data decreases below a specified threshold ellipticity value.

Alternatively, ellipticity of data from physiologic signals representative of dissimilar physiology will increase as HF worsens. In this case, an indication of worsening HF can be provided when the ellipticity of the data increases above a specified threshold ellipticity value.

Figure 6:
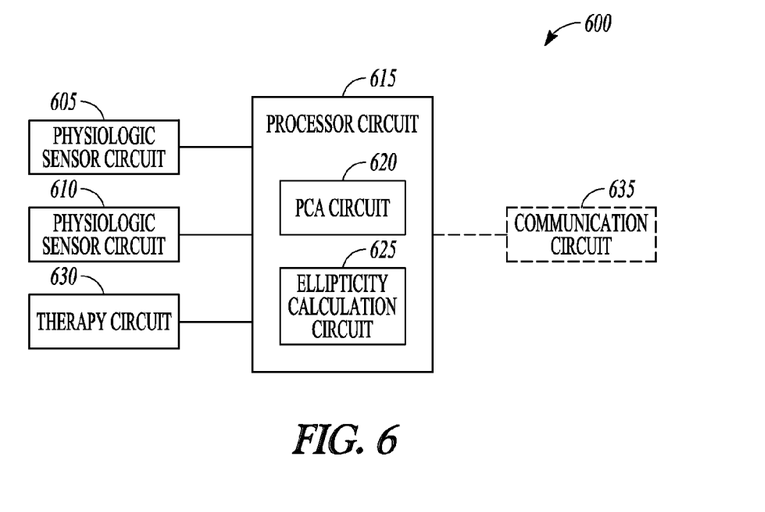
FIG. 6 is a block diagram of portions of an example of an implantable or ambulatory medical device that monitors HF failure of a subject.

FIG. 6 is a block diagram of portions of an example of an implantable or ambulatory medical device 600 that monitors HF of a subject. The device 600 includes at least a first physiologic sensor circuit 605 and a second physiologic sensor circuit 610. The first physiologic sensor circuit 605 is configured to provide a first physiologic signal and the second physiologic sensor circuit 610 is configured to provide a second physiologic signal.

The device 600 also includes a processor circuit 615 communicatively coupled to the first and second physiologic sensor circuits. The communicative coupling allows electrical signals to be communicated between the sensor circuits and the processor circuit 615 even though there may be one or more intervening circuits between the sensor circuits and the processor circuit 615. For example, the device 600 may include a sampling circuit (not shown) integral to the processor circuit 615 or electrically coupled between the sensor circuits and the processor circuit 615. The sampling circuit is configured to sample the physiologic signals to produce physiologic data.

The processor circuit 615 can be a microprocessor, a digital signal processor, application specific integrated circuit (ASIC), microprocessor, or other type of processor, interpreting or executing instructions in software modules or firmware modules. The processor circuit 615 includes other circuits or sub-circuits to perform the functions described. These circuits may include software, hardware, firmware or any combination thereof. Multiple functions can be performed in one or more of the circuits as desired.

The processor circuit 615 includes a principal component analysis (PCA) circuit 620 that represents data determined from the first physiologic sensor circuit 605 as a first axis in a multidimensional space and represents data determined from the second physiologic sensor circuit 610 as a second axis in the multidimensional space. There is no requirement that these axes be displayed.

Figure 7:
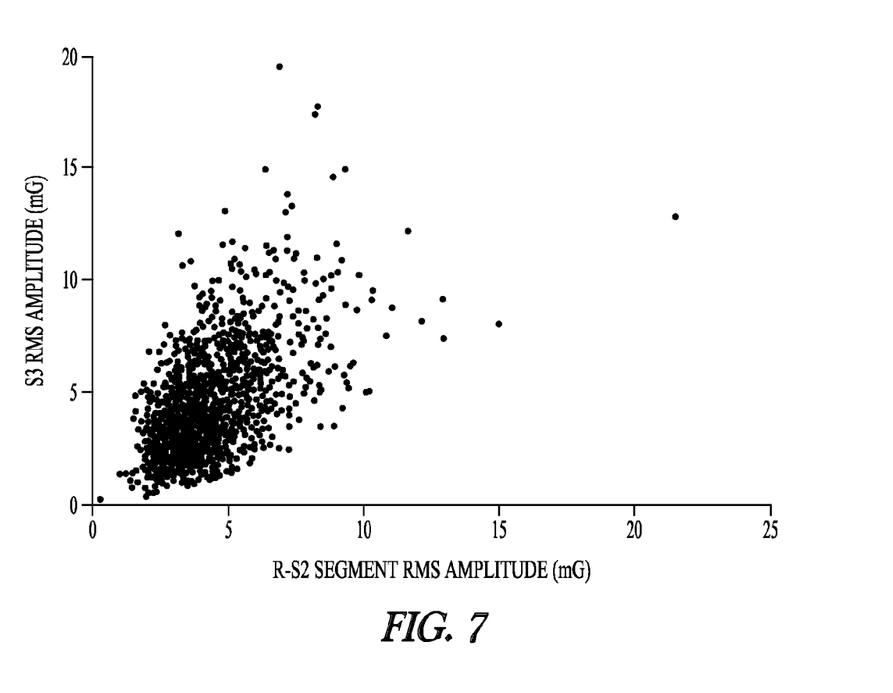
FIG. 7 shows an illustration of an example of data represented in a multidimensional space.

FIG. 7 shows an illustration of an example of data represented in a multidimensional space. In the example, the first physiologic sensor signal is representative of the root mean square (RMS) amplitude of an S3 heart sound and the S3 RMS amplitude is the first axis in the multidimensional space. The signals may be provided by first and second heart sound sensors or by the same heart sound sensor.

The second physiologic sensor signal is representative of the RMS amplitude of a segment of a heart sound signal that starts at the occurrence of an R-wave and ends at the occurrence of the S2 heart sound (e.g., an R-S2 signal segment). An R-wave is a part of an electrogram or electrocardiogram that is representative of ventricular depolarization. In some examples, the device 600 includes a third physiologic sensor circuit (not shown) that includes a cardiac signal sensing circuit. R-waves can be sensed by the cardiac signal sensing circuit concurrently with sensing of the heart sounds to determine the start of the heart sound signal segment. The R-S2 signal segment RMS amplitude is the second axis in the multidimensional space. A data cloud in the multidimensional space of FIG. 7 is formed by the represented data.

The PCA circuit 620 also determines a plurality of principal components in the multidimensional space. The PCA circuit 620 may calculate the principal components using any of the methods described herein, such as by using one or more of an eigenvector transform and the KLT or the Hotelling transform. In some examples, the principal components are determined after data has been collected for a specified period of time. In some examples, the processor circuit 615 initiates PCA by the PCA circuit 620 according to a specified schedule, such as by time of day.

The PCA circuit 620 also determines a quantitative attribute of the first and the second physiologic signals using the determined principal components or a projection of the data along the determined principal components. In some examples, the processor circuit 615 includes an ellipticity calculation circuit 625 that calculates the ellipticity of the data cloud formed in the multidimensional space as the quantitative attribute. In the example of FIG. 7, the eigenvalues are 6.4673 and 1.3613, and the ellipticity of the data cloud is 0.8261.

In some examples, the ellipticity calculation circuit 625 calculates a plurality of eigenvalues corresponding to the plurality of principal components in the multidimensional space and calculates ellipticity using the eigenvalues, such as by using equation (3).

The calculation can be generalized from the two dimensional case to the case of N physiologic sensor circuits configured to provide N physiologic signals. Output from the N physiologic sensor circuits is represented as N axes in the multidimensional space. N principal components are calculated in the N-dimensional space and the ellipticity calculation circuit 625 calculates the quantitative attribute of the N physiologic signals such as by calculating the ellipticity of the data in the multidimensional space.

As described previously, the value of the calculated ellipticity can change as the HF of the subject worsens. In some examples, the first physiologic signal is representative of an aspect of physiology of the subject that is similar to an aspect of physiology represented by the second physiologic signal. The PCA circuit 620 is configured to provide an indication of worsening HF of the subject when detecting a decrease in calculated ellipticity, or detecting a change (e.g., a negative change) in calculated ellipticity greater than a specified ellipticity change value.

Physiologic signals representing similar aspects of physiology include different metrics provided by the same type of sensor. In some examples, the physiologic sensor circuits include one or more heart sound sensor circuits, and the first physiologic sensor signal is representative of a parameter of a heart sound and the second physiologic sensor signal is representative of a parameter of a different heart sound. A non-exhaustive list of examples of parameters include the amplitude of heart sound, the duration of a heart sound, a time interval from a first specified event to the occurrence of a heart sound. An example is shown in FIG. 7 where the first physiologic signal is the RMS amplitude of the S3 heart sound and the second physiologic signal is the amplitude of the R-S2 segment of a heart sound signal.

In some examples, the physiologic sensor circuits representing similar aspects of physiology include one or more impedance sensor circuits, and the first physiologic signal and the second physiologic signal are representative of, or derived from, impedance signals provided by the impedance sensor circuits. Impedance can be measured between combinations of electrodes, such as between electrodes in the example electrode arrangement of FIG. 1. An impedance signal can be measured within the heart (intracardiac impedance), such as the impedance measured between tip electrode 135 and SVC electrode 180 in FIG. 1. Impedance measured within the heart changes with the filling and emptying of the chambers. This impedance can be used to measure cardiac stroke volume. As described previously, impedance can also be measured between an electrode on a lead and an electrode formed on the can of the IMD to measure impedance in the thorax region of the subject (e.g., ITTI).

An arrangement of electrodes such as those shown in the example of FIG. 1 can be used to measure impedance in multiple directions. This is sometimes called measuring impedance vectors. For example, impedance measured between coil electrode 175 and an electrode formed on the can or header of the IMD can be a first impedance vector, and impedance measured between the ring electrode 160 and an electrode formed on the can or header of the IMD can be a second impedance vector. In FIG. 6, the first physiologic signal can be a first impedance signal measured in a first direction (e.g., a first impedance vector to measure ITTI) and the second impedance signal measured in a direction different from the first impedance signal (e.g., a second impedance vector to measure ITTI).

ITTI or thoracic impedances are sensitive to thoracic fluid. During stable HF, patients follow a deterministic circadian pattern such that they are mostly upright throughout the day and mostly supine throughout the night. Supine postures driving fluid from the extremities into the thorax causing thoracic impedances to decrease, whereas upright posture drain fluid from the thorax into lower extremities causing impedances to increase. These deterministic impedance responses to diurnal postural changes serve as a common driving force that causes a strong relationship between multiple thoracic impedance vectors. However, during worsening HF patients may be inclined to be recumbent most of the time, thus, abolishing the circadian postural drive. This may result in weakening of the relationship between multiple thoracic impedances leading up to worsening HF.

In some examples, the physiologic sensor circuits include one or more respiration sensor circuits, and the first physiologic signal and the second physiologic signal are representative of respiration signals provided by, or derived from, the respiration sensor circuits. In some examples, the first physiologic signal can include respiration rate (RR) and the second physiologic signal can include respiration tidal volume (TV), or the first physiologic signal can include respiration rate (RR) and the second physiologic signal can include minute ventilation (MV, where MV=TV×RR).

Data determined from the first physiologic sensor circuit is represented as a first axis in the multidimensional space. In some examples, the first axis is a first statistical measure of the output of a physiological sensor circuit and the second axis is a second statistical measure of the output of the physiologic sensor circuit. A non-exhaustive list of examples includes a minimum value of a physiologic signal provided by the sensor, the maximum value of a physiologic signal, a mean value of a physiologic sensor, and a median value of a physiologic signal.

In some examples, the first physiologic signal is representative of an aspect of physiology of the subject that is dissimilar to, or disparate from, an aspect of physiology represented by the second physiologic signal. The PCA circuit 620 is configured to provide an indication of worsening HF of the subject when detecting an increase in the ellipticity, or a change in calculated ellipticity greater than a specified ellipticity change value. If the ellipticity decreases after the detected increase, this subsequent decrease may indicate that HF of the subject has become stable.

Physiologic signals representing dissimilar aspects of physiology include metrics provided from different types of sensor. In some examples, the physiologic sensor circuits 605, 610 include an impedance sensor, a heart sound sensor, a cardiovascular pressure sensor, and an activity sensor.

An example of an activity sensor includes an accelerometer. The accelerometer can be included in an ambulatory device or included in an electronics unit contained in an IMD can. An example of a cardiovascular pressure sensor includes a sensor implantable in a coronary vessel to determine left ventricle pressure by direct measurement of coronary vessel pressure. A description of systems and methods that use such an implantable pressure sensor is found in Salo et al., U.S. Pat. No. 6,666,826, entitled "METHOD AND APPARATUS FOR MEASURING LEFT VENTRICULAR PRESSURE," filed Jan. 4, 2002, which is incorporated herein by reference in its entirety. Other cardiovascular pressure sensor examples include a right ventricle (RV) pressure sensor, a pulmonary artery pressure sensor, a left or right atrial pressure sensor, and estimate of left ventricle end diastolic pressure (LVEDP).

An example of dissimilar physiologic signals includes a physiologic signal representative of ITTI and a physiologic signal representative of cardiovascular pressure. Since thoracic impedance reflects thoracic fluid status, they reflect a disparate aspect of physiology than parameters that may represent cardiac filling status (such as filling pressures). As a result, a weak relationship may be expected between the two during stable HF. However, during worsening HF, cardiac filling pressures are elevated. These elevated filling pressures gradually build up a backlog of fluid in the lungs, which eventually may lead to pulmonary edema. This fluid back up in the lungs causes a decrease in thoracic impedance. Thus, during worsening HF there is a more direct causal relationship between filling pressures and thoracic fluid status.

Hence, thoracic impedance and measures of filling pressures may show an increased relationship leading up to HF decompensation.

Figure 8A:
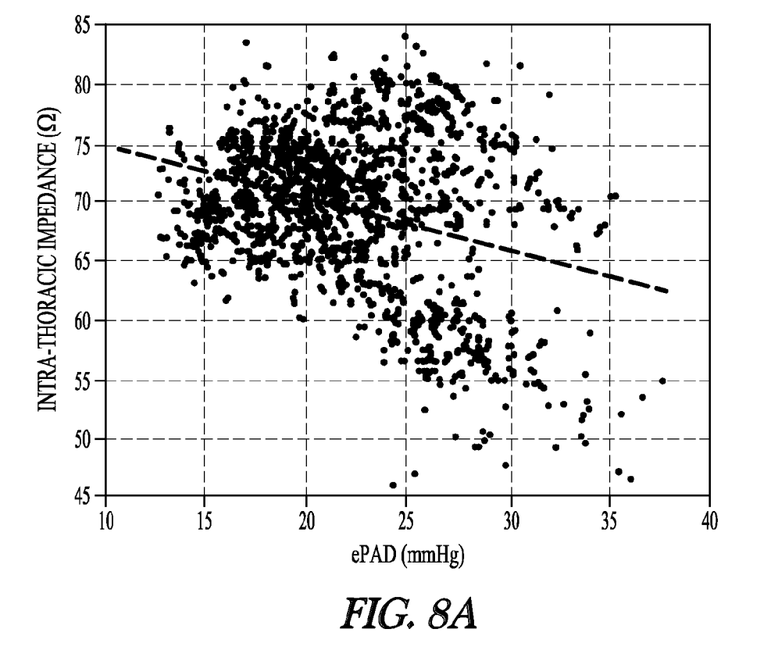
FIGS. 8A and 8B show an example of intra-thoracic impedance data and estimate of pulmonary artery diastolic (ePAD) pressure data represented in a multidimensional space.
Figure 8B:
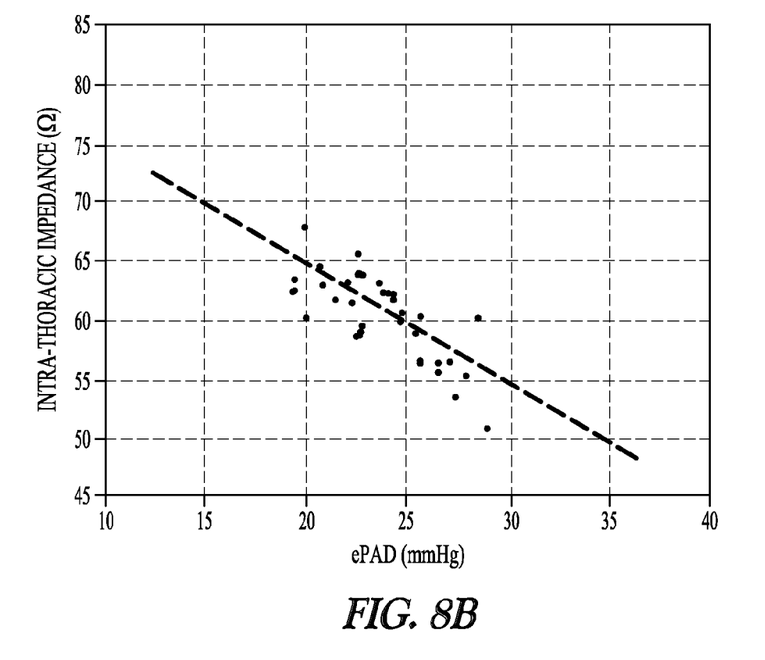

FIGS. 8A and 8B show examples of intra-thoracic impedance data and estimate of pulmonary artery diastolic (ePAD) pressure data represented in a multidimensional space. The data in FIG. 8A shows a low degree of ellipticity due to the dissimilar nature intra-thoracic impedance and ePAD. The data in FIG. 8B is after a minor HF event. It can be seen in FIG. 8B that the degree of ellipticity increased with the HF event.

Other quantitative attributes derived from principal components are useful instead of, or in addition to, ellipticity. According to some examples, the PCA circuit 620 of FIG. 6 is configured to determine, as the quantitative attribute, an orientation of at least one of the principal components in the multidimensional space. The PCA circuit 620 is configured to provide an indication of worsening HF when detecting a shift in the orientation that is outside of a specified orientation range. Stated another way, for a group of physiologic sensors where the relationship among the data obtained from the sensors changes with worsening HF, a shift in the orientation of the principal components in the multidimensional space is beyond a shift any normal variation of the orientation that would be expected.

Figure 9:
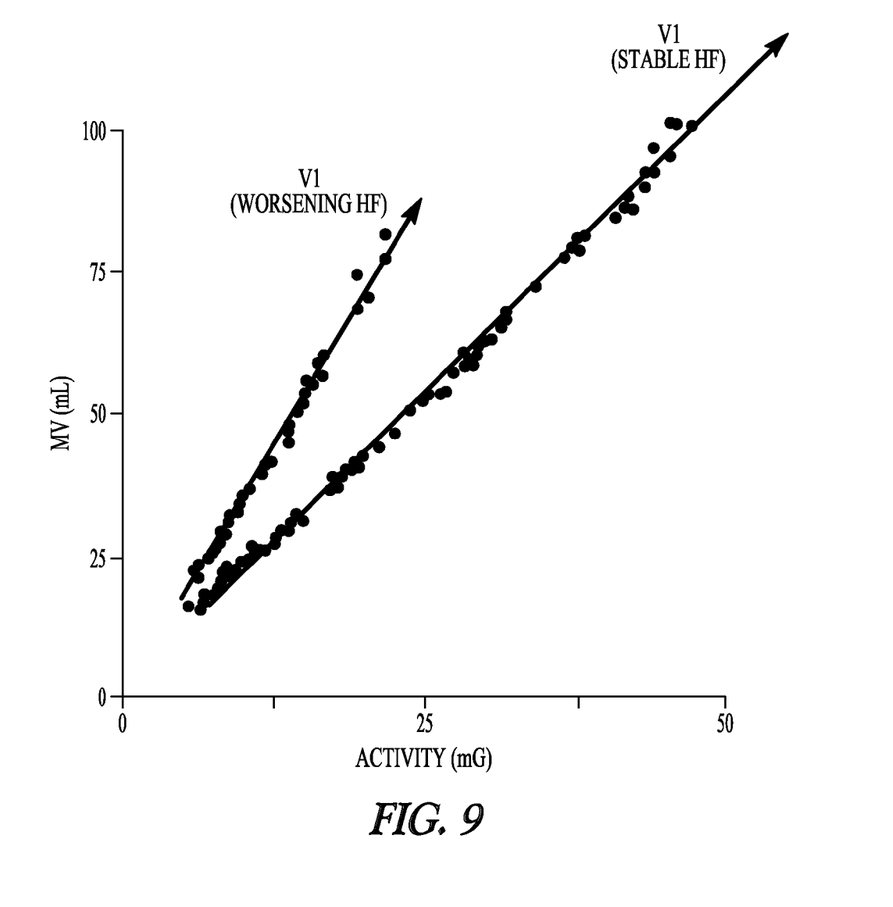
FIG. 9 shows an example of a shift in orientation of a principal component in a multidimensional space.

An illustrative example is shown in FIG. 9, the first physiologic signal can be representative of MV and the second physiologic signal can be representative of activity of the subject. For stable periods of HF, an increase in activity will be accompanied by an increase in MV. Thus, the two physiologic signals would show some relationship during stable HF. The first principal component V1 (the principal component associated with the largest eigenvalue) is shown having a first direction during stable HF. With worsening HF, an increase in MV may occur without an increase in activity and may occur even with decreased activity. Thus, the two physiologic signals show a different relationship during worsening HF, and hence, the direction of V1 can change drastically when HF worsens. In some examples, the PCA circuit 620 is configured to provide an indication of worsening HF of the subject when detecting a shift in orientation of the principal component associated with the largest eigenvalue that is greater than a specified threshold orientation shift value.

The PCA circuit 620 provides an indication of heart failure (HF) according to the quantitative attribute to at least one of a user or a process. In some examples, the device 600 is an ambulatory device and includes a display. The processor circuit 615 may execute a process to display the indication of HF to a user on the display. In some examples, the device 600 is an implantable device and communicates wirelessly with a second device using a communication circuit 635, such as by RF or inductive telemetry. The second device may have a display to present the indication of HF to a user.

According to some examples, the device 600 includes a therapy circuit 630 configured to deliver therapy to the subject. In some examples, the therapy circuit 630 provides pacing therapy to the subject. The processor circuit 615 may change a device therapy parameter based on the indication from the PCA circuit 620. For instance, if the PCA provides an indication of worsening HF, the processor circuit 615 may change the timing of inter-ventricular pacing to adjust synchronization of the ventricles, or the processor circuit 615 may change the timing of intra-ventricular pacing to try and improve ventricular contractions.

Figure 10:
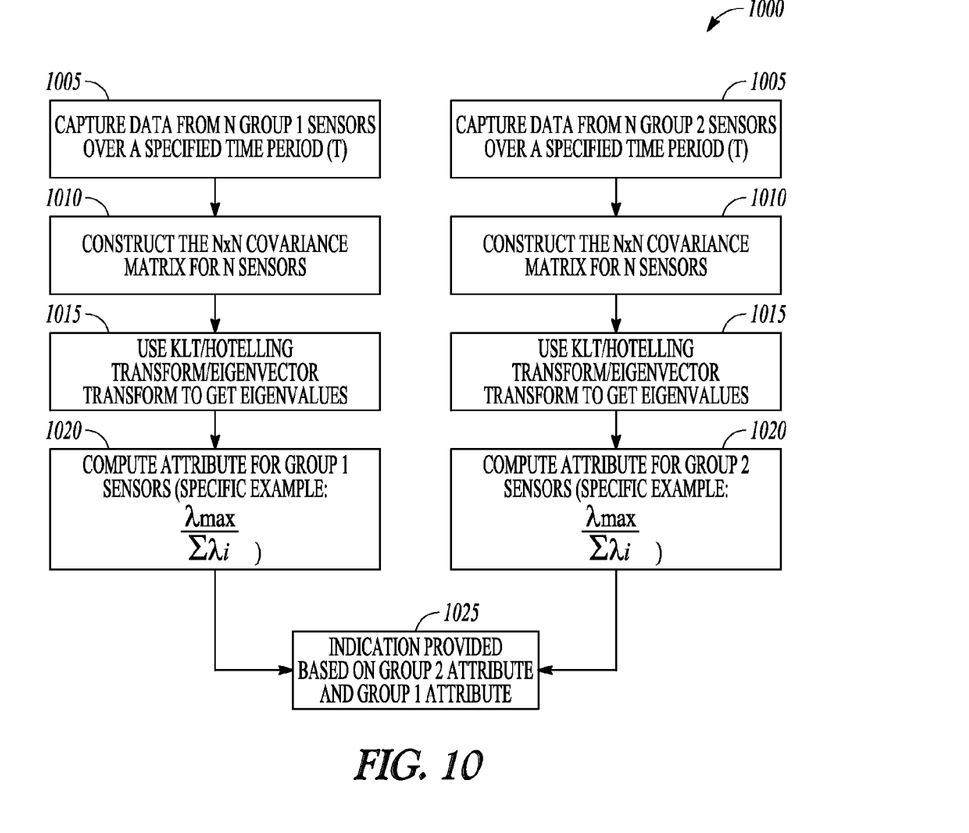
FIG. 10 is a flow diagram of an example of a method of performing PCA on multiple groups of sensors.

PCA can be performed on more than one group of sensors. FIG. 10 is a flow diagram of an example of a method 1000 of performing PCA on multiple groups of sensors. At block 1005, data is collected using N sensors in Group 1 and N sensors in Group 2. The number of sensors does not have to be the same in each group. The data is collected for a specified period of time (e.g., several hours).

At block 1010, covariance matrices are constructed for the sensor data in each group. The matrices have dimensions of N×N corresponding to the N sensors. At block 1015, the eigenvalues of the principal components are determined using KLT. At block 1020, a first quantitative attribute (e.g., ellipticity) is determined for the data from the Group 1 sensors and a second quantitative attribute is determined for the data from the Group 2 sensors. The first and second attributes may be the same attribute or may be different attributes.

At block 1025, an indication of HF is provided based on the first and second quantitative attributes. This method can be generalized beyond two groups of sensors to M groups of sensors. The indication of HF is based on at least a portion of M quantitative attributes determined for the M groups.

The groups of sensors may include one or more groups of sensors that relate to similar aspects of physiology and one or more groups of sensors that relate to dissimilar aspects of physiology.

Returning to FIG. 6, in some examples the first physiologic signal and the second physiologic signal are representative of similar aspects of physiology of the subject. The device includes at least a third physiologic sensor circuit configured to provide a third physiologic signal and a fourth physiologic sensor circuit configured to provide a fourth physiologic signal. The third physiologic signal is representative of an aspect of physiology of the subject that is dissimilar to an aspect of physiology represented by the fourth physiologic signal.

The PCA circuit 620 represents output from the first physiologic sensor and the second physiologic sensor as a first axis and a second axis, respectively, in a first multidimensional space, and represents output from the third physiologic sensor and the fourth physiologic sensor as a first axis and a second axis, respectively, in a second multidimensional space. The PCA circuit 620 determines a first quantitative attribute of the first physiologic signal and the second physiologic signal using the first multidimensional space and determines a second quantitative attribute of the third physiologic signal and the fourth physiologic signal using the second multidimensional space.

The PCA circuit 620 provides an indication of HF according to the quantitative attribute determined using the first multidimensional space and the quantitative attribute determined using the second multidimensional space. It is possible that the quantitative attributes may not agree whether the HF of the subject is stable or increasing. The PCA circuit 620 may apply a weight to the quantitative attributes to resolve any ambiguity. For example, the PCA circuit 620 may give greater weight to a group of sensors relating to similar physiology than to a group of sensors relating to dissimilar physiology, or vice versa. In some examples, the number of groups of sensors is an odd number and a majority result is used as the indication of HF.

In some examples, the first quantitative attribute and the second quantitative attribute can be different types. For instance, the first quantitative attribute may be ellipticity and the second quantitative attribute may be an orientation of at least one of the principal components in the multi-dimensional space. The PCA circuit 620 may apply different weight to the different types of quantitative attributes to assess HF of the subject.

If the device 600 is an IMD, it may be desirable to offload the calculations executed for the PCA onto a second device to conserve battery power or to reduce the complexity of the IMD. The second device may be an IMD programmer or the second device may be a server that communicates with the IMD via a third device such as a repeater placed in the vicinity of the subject.

In some examples, the PCA circuit 620 is included in the second device. The device 600 includes a communication circuit 635 to communicate data obtained from the physiologic sensor circuits to the second device for PCA and may determine the quantitative attribute. The second device generates the indication of HF using the quantitative attribute and may display the indication to a user provide the indication to a process, or both display the indication and provide the indication to a process. The second device may communicate the indication to the IMD and the IMD may alter its operation (e.g., alter therapy or alter sensing capability) due to the indication of HF. In some examples, the second device alters the operation of the IMD by communicating operational parameters to the IMD.

The methods and devices described herein show that PCA performed by a medical device can be a useful tool to forming a composite predictor of progression of HF.

ADDITIONAL NOTES AND EXAMPLES

Example 1 includes subject matter (such as an apparatus) comprising at least a first physiologic sensor circuit configured to provide a first physiologic signal and a second physiologic sensor circuit configured to provide a second physiologic signal, wherein a physiologic signal includes physiological information of a subject, and a processor circuit. The processor circuit is communicatively coupled to the first and second physiologic sensor circuits and includes a PCA circuit configured to represent data determined from the at least first and second physiologic sensor circuits as at least first and second axes, respectively, in a multidimensional space, determine one or more principal components in the multidimensional space, determine a quantitative attribute of the first and the second physiologic signals using at least one of the determined principal components or a projection of the data along the at least one determined principal component, and provide an indication of HF status according to the quantitative attribute to at least one of a user or a process.

In Example 2, the PCA circuit of Example 1 can optionally include an ellipticity calculation circuit configured to calculate, as the quantitative attribute, ellipticity of a data cloud formed by representing the data from the first and second physiologic signals in the multi-dimensional space, and provide the indication of HF according to the calculated ellipticity.

In Example 3, the ellipticity calculation circuit of one or any combination of claims 1 and 2 can optionally be configured to calculate a plurality of eigenvalues corresponding to the principal components in the multidimensional space and calculate ellipticity using the plurality of eigenvalues.

In Example 4, the first physiologic signal of one or any combination of Examples 1-3 can optionally be representative of an aspect of physiology of the subject that is dissimilar to an aspect of physiology represented by the second physiologic signal, and the PCA circuit can be optionally configured to provide an indication of worsening HF of the subject when detecting an increase in the ellipticity.

In Example 5, the first physiologic sensor circuit and the second physiologic sensor circuit of one or any combination of Examples 1-4 can optionally include at least two of: an impedance sensor, a respiration sensor, a heart sound sensor, a cardiovascular pressure sensor, and an activity sensor.

In Example 6, the PCA circuit of one or any combination of Examples 1-5 can optionally be configured to provide an indication of stable HF of the subject when detecting that the ellipticity decreases below a specified ellipticity threshold value.

In Example 7, the first physiologic signal of one or any combination of Examples 1-6 can optionally be representative of an aspect of physiology of the subject that is similar to an aspect of physiology represented by the second physiologic signal, and the PCA circuit can optionally be configured to provide an indication of worsening HF of the subject when detecting a decrease in the ellipticity.

In Example 8, the PCA circuit of one or any combination of Examples 1-7 can optionally be configured to represent a first axis and a second axis of the multidimensional space as at least one of a first impedance signal and a second impedance signal measured in a direction different from the first impedance signal, an amplitude of a heart sound and an amplitude of a different heart sound, respiration rate and tidal volume, and a first statistical measure of an output of a physiological sensor and a second statistical measure of the output of the physiologic sensor.

In Example 9, the subject matter of one or any combination of Examples 1-8 can optionally include at least a third physiologic sensor circuit configured to provide a third physiologic signal and a fourth physiologic sensor circuit configured to provide a fourth physiologic signal, wherein the third physiologic signal is representative of an aspect of physiology of the subject that is dissimilar to an aspect of physiology represented by the fourth physiologic signal. The PCA circuit can optionally be configured to represent output from the third physiologic sensor and the fourth physiologic sensor as a first axis and a second axis, respectively, in a second multidimensional space, determine a quantitative attribute of the third physiologic signal and the fourth physiologic signal using the second multidimensional space, and provide an indication of HF according to the quantitative attribute determined using the first multidimensional space and the quantitative attribute determined using the second multidimensional space.

In Example 10, the PCA circuit of one or any combination of Examples 1-9 can optionally be configured to determine, as the quantitative attribute, an orientation of one or more of the principal components in the multi-dimensional space, and provide an indication of worsening HF of the subject when detecting a shift in the orientation outside of a specified orientation range.

In Example 11, the subject matter of one or any combination of Examples 1-10 optionally includes N physiologic sensor circuits configured to provide N physiologic signals, wherein N is an integer. The PCA circuit can optionally be configured to represent output from the N physiologic sensor circuits as N axes in the multidimensional space, and determine a quantitative attribute of the N physiologic signals using the multidimensional space.

Example 12 can include subject matter, or can optionally be combined with the subject matter of one or any combination of Examples 1-11 to include subject matter (such as a method, a means for performing acts, or a machine-readable medium including instructions that, when performed by the machine, cause the machine to perform acts), comprising sensing at least a first physiologic signal using a first physiologic sensor circuit and a second physiologic signal using a second physiologic sensor circuit, wherein a physiologic signal includes physiological information of a subject, representing data determined from the at least first physiologic signal and second physiologic signal as at least a first axis and a second axis, respectively, in the multidimensional space, determining one or more principal components of the data represented in the multidimensional space, determining a quantitative attribute of the data from the first and second physiologic signals using at least one of the determined principal components or a projection of the data along at least one of the determined principal components, and providing an indication of HF status to at least one of a user or a process according to the quantitative attribute.

In Example 13, the quantitative attribute of Example 12 can optionally include a measure of ellipticity of a data cloud formed by representing the data from the first and second physiologic signals in the multi-dimensional space.

In Example 14, the subject matter of one or any combination of Examples 12 and 13 can optionally include calculating a plurality of eigenvalues corresponding to the principal components in the multidimensional space and the calculating a measure of ellipticity optionally includes calculating ellipticity using the plurality of eigenvalues.

In Example 15, the first physiologic signal of one or any combination of Examples 12-15 can optionally represent an aspect of physiology of the subject that is dissimilar to an aspect of physiology represented by the second physiologic signal, and the providing an indication of heart failure according to the quantitative attribute can optionally include indicating worsening HF of the subject when detecting an increase in the quantitative attribute.

In Example 16, the first physiologic signal and the second physiologic signal of one or any combination of Examples 12-15 can optionally be representative of any two of: impedance, a heart sound, cardiovascular pressure, and activity.

In Example 17, the first physiologic signal of one or any combination of Examples 12-16 can optionally represent an aspect of physiology of the subject that is similar to an aspect of physiology represented by the second physiologic signal, and the providing an indication of heart failure according to the quantitative attribute can optionally include indicating worsening HF of the subject when detecting a decrease in the quantitative attribute.

In Example 18, the first axis and the second axis of the multidimensional space of one or any combination of Examples 12-17 can optionally represent at least one of a first impedance signal and a second impedance signal measured in a direction different from the first impedance signal, an amplitude of a heart sound and an amplitude of a different heart sound, respiration rate and tidal volume, and a first statistical measure of an output of a physiological sensor and a second statistical measure of the output of the physiologic sensor.

In Example 19, the subject matter of one or any combination of Examples 12-18 can optionally include sensing at least a third physiologic signal using a third physiologic sensor circuit and a fourth physiologic signal using a fourth physiologic sensor circuit, wherein the third physiologic signal represents an aspect of physiology of the subject that is dissimilar to an aspect of physiology represented by the fourth physiologic signal, representing output from the third physiologic sensor and the fourth physiologic sensor as first and second axes, respectively, in a second multidimensional space, and determining a quantitative attribute of the third physiologic signal and the fourth physiologic signal using the second multidimensional space. The providing an indication of HF can optionally include providing an indication of HF according to the quantitative attribute determined using the first multidimensional space and the quantitative attribute determined using the second multidimensional space.

In Example 20, the quantitative attribute of one or any combination of Examples 1-19 can optionally include an orientation of one or more of the principal components in the multi-dimensional space, and the providing an indication of heart failure can optionally include providing an indication of worsening HF of the subject when detecting a shift in the orientation outside of a specified orientation range.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting Examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable or other ambulatory apparatus comprising:
   at least a first physiologic sensor circuit, configured to provide a first physiologic signal and a second physiologic sensor circuit configured to provide a second physiologic signal, wherein the first and second physiologic signals include physiological information of a subject;
   a processor circuit, communicatively coupled to the first and second physiologic sensor circuits, wherein the processor circuit includes a principal component analysis (PCA) circuit configured to:
      represent data determined from the at least first and second physiologic sensor circuits as at least first and second axes, respectively, in a multidimensional space;
      determine one or more principal components in the multidimensional space;
      determine a quantitative attribute of the first and second physiologic signals using at least one of the determined principal components or a projection of the data along the at least one determined principal component; and
      provide an indication of heart failure (HF) status according to the quantitative attribute to at least one of a user or a process.

2. The apparatus of claim 1, wherein the PCA circuit includes an ellipticity calculation circuit configured to:
   calculate, as the quantitative attribute, ellipticity of a data cloud formed by representing the data from the first and second physiologic signals in the multi-dimensional space; and
   provide the indication of HF according to the calculated ellipticity.

3. The apparatus of claim 2, wherein the ellipticity calculation circuit is configured to:
   calculate a plurality of eigenvalues corresponding to the principal components in the multidimensional space; and
   calculate ellipticity using the plurality of eigenvalues.

4. The apparatus of claim 2,
   wherein the first physiologic signal is representative of an aspect of physiology of the subject that is dissimilar to an aspect of physiology represented by the second physiologic signal, and
   wherein the PCA circuit is configured to provide an indication of worsening HF of the subject when detecting an increase in the ellipticity.

5. The apparatus of claim 4, wherein the first physiologic sensor circuit and the second physiologic sensor circuit include at least two of: an impedance sensor, a respiration sensor, a heart sound sensor, a cardiovascular pressure sensor, and an activity sensor.

6. The apparatus of claim 4, wherein the PCA circuit is configured to provide an indication of stable HF of the subject when detecting that the ellipticity decreases below a specified ellipticity threshold value.

7. The apparatus of claim 2,
   wherein the first physiologic signal is representative of an aspect of physiology of the subject that is similar to an aspect of physiology represented by the second physiologic signal, and
   wherein the PCA circuit is configured to provide an indication of worsening HF of the subject when detecting a decrease in the ellipticity.

8. The apparatus of claim 7, wherein the PCA circuit is configured to represent a first axis and a second axis of the multidimensional space as at least one of:
   a first impedance signal and a second impedance signal measured in a direction different from the first impedance signal;
   an amplitude of a heart sound and an amplitude of a different heart sound;
   respiration rate and tidal volume; and
   a first statistical measure of an output of a physiological sensor and a second statistical measure of the output of the physiologic sensor.

9. The apparatus of claim 7, including:
   at least a third physiologic sensor circuit configured to provide a third physiologic signal and a fourth physiologic sensor circuit configured to provide a fourth physiologic signal, wherein the third physiologic signal is representative of an aspect of physiology of the subject that is dissimilar to an aspect of physiology represented by the fourth physiologic signal;
   wherein the PCA circuit is configured to:
   represent output from the third physiologic sensor and the fourth physiologic sensor as a first axis and a second axis, respectively, in a second multidimensional space;
   determine a quantitative attribute of the third physiologic signal and the fourth physiologic signal using the second multidimensional space; and
   provide an indication of HF according to the quantitative attribute determined using the first multidimensional space and the quantitative attribute determined using the second multidimensional space.

10. The apparatus of claim 1, wherein the PCA circuit is configured to:
    determine, as the quantitative attribute, an orientation of one or more of the principal components in the multidimensional space; and
    provide an indication of worsening HF of the subject when detecting a shift in the orientation outside of a specified orientation range.

11. The apparatus of claim 1, including:
    N physiologic sensor circuits configured to provide N physiologic signals, wherein N is an integer, wherein the PCA circuit is configured to:
represent output from the N physiologic sensor circuits as N axes in the multidimensional space; and
determine a quantitative attribute of the N physiologic signals using the multidimensional space.

12. A method of operating an implantable or other ambulatory medical device, the method comprising:
sensing at least a first physiologic signal using a first physiologic sensor circuit and a second physiologic signal using a second physiologic sensor circuit, wherein the first and second physiologic signals include physiological information of a subject;
representing, using a processor circuit including a principal component analysis (PCA) circuit, data determined from the at least first physiologic signal and second physiologic signal as at least a first and a second axis, respectively, in a multidimensional space;
determining, using the processor circuit, one or more principal components of the data represented in the multidimensional space;
determining, using the processor circuit, a quantitative attribute of the data form the first and second physiologic signals using a least one of the one or more determined principal components or a projection of the data along the at least one determined principal component; and
providing, using the processor circuit, an indication of heart failure (HF) status to at least one of a user of a process according to the quantitative attribute.

13. The method of claim 12, wherein the quantitative attribute includes a measure of ellipticity of a data cloud formed by representing the data from the first and second physiologic signals in the multi-dimensional space.

14. The method of claim 13, including:
calculating a plurality of eigenvalues corresponding to the principal components in the multidimensional space; and
wherein calculating a measure of ellipticity includes calculating ellipticity using the plurality of eigenvalues.

15. The method of claim 13,
wherein the first physiologic signal represents an aspect of physiology of the subject that is dissimilar to an aspect of physiology represented by the second physiologic signal, and
wherein providing an indication of heart failure according to the quantitative attribute includes indicating worsening HF of the subject when detecting an increase in the quantitative attribute.

16. The method of claim 15, wherein the first physiologic signal and the second physiologic signal are representative of any two of: impedance, a heart sound, cardiovascular pressure, and activity.

17. The method of claim 13,
wherein the first physiologic signal represents an aspect of physiology of the subject that is similar to an aspect of physiology represented by the second physiologic signal, and
wherein providing an indication of heart failure according to the quantitative attribute includes indicating worsening HF of the subject when detecting a decrease in the quantitative attribute.

18. The method of claim 17, wherein the first axis and the second axis of the multidimensional space represent at least one of:
a first impedance signal and a second impedance signal measured in a direction different from the first impedance signal;
an amplitude of a heart sound and an amplitude of a different heart sound;
respiration rate and tidal volume; and
a first statistical measure of an output of a physiological sensor and a second statistical measure of the output of the physiologic sensor.

19. The method of claim 17, including:
sensing at least a third physiologic signal using a third physiologic sensor circuit and a fourth physiologic signal using a fourth physiologic sensor circuit, wherein the third physiologic signal represents an aspect of physiology of the subject that is dissimilar to an aspect of physiology represented by the fourth physiologic signal;
representing output from the third physiologic sensor and the fourth physiologic sensor as first and second axes, respectively, in a second multidimensional space;
determining a quantitative attribute of the third physiologic signal and the fourth physiologic signal using the second multidimensional space; and
wherein providing an indication of HF includes providing an indication of HF according to the quantitative attribute determined using the first multidimensional space and the quantitative attribute determined using the second multidimensional space.

20. The method of claim 13,
wherein the quantitative attribute includes an orientation of one or more of the principal components in the multidimensional space, and
wherein providing an indication of heart failure includes providing an indication of worsening HF of the subject when detecting a shift in the orientation outside of a specified orientation range.

* * * * *